(12) United States Patent
van Aggelen

(10) Patent No.: US 11,901,044 B2
(45) Date of Patent: Feb. 13, 2024

(54) SYSTEM AND METHOD FOR DETERMINING SUFFICIENCY OF GENOMIC SEQUENCING

(71) Applicant: KONINKLIJKE PHILIPS N.V., Eindhoven (NL)

(72) Inventor: Helen Cecile van Aggelen, Berkeley, CA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 995 days.

(21) Appl. No.: 16/739,784

(22) Filed: Jan. 10, 2020

(65) Prior Publication Data

US 2020/0227140 A1    Jul. 16, 2020

Related U.S. Application Data

(60) Provisional application No. 62/792,991, filed on Jan. 16, 2019.

(51) Int. Cl.
| | |
|---|---|
| G16B 40/10 | (2019.01) |
| C12Q 1/6869 | (2018.01) |
| G06F 12/0853 | (2016.01) |
| G16B 50/30 | (2019.01) |
| G16B 30/00 | (2019.01) |

(52) U.S. Cl.
CPC ........... *G16B 40/10* (2019.02); *C12Q 1/6869* (2013.01); *G06F 12/0853* (2013.01); *G16B 30/00* (2019.02); *G16B 50/30* (2019.02)

(58) Field of Classification Search
None
See application file for complete search history.

(56) References Cited

U.S. PATENT DOCUMENTS

| | | |
|---|---|---|
| 9,845,552 B2 | 12/2017 | Blume et al. |
| 2011/0257889 A1 | 10/2011 | Chaisson et al. |
| 2016/0132640 A1 | 5/2016 | Layer et al. |

OTHER PUBLICATIONS

Melsted P, Pritchard JK. 2011. Efficient counting of k-mers in DNA sequences using a bloom filter. BMC Bioinformatics 12(333): 1-7. (Year: 2011).*
Choi CS. 2016. On the study of microbial transcriptomes using second and third-generation sequencing technologies. Journal of Microbiology 54(8); 527-536.DOI 10.1007/s12275-016-6233-2 (Year: 2016).*
Aggarwal CC. 2015. Data Mining: The Textbook. Springer: New York. 746 pp. (Year: 2015).*
Hartlmüller C, Göbl C, Madl T. Prediction of protein structure using surface accessibility data. Angew. Chem. Int. Ed. 2016, 55, 11970. (Year: 2016).*
Holley G, Wittler R, Stoye J. Bloom Filter Trie: an alignment-free and reference-free data structure for pan-genome storage. Algorithms Mol Biol 11, 3 (2016). https://doi.org/10.1186/s13015-016-0066-8 (Year: 2016).*
Chikhi R, Rizk G. Space-efficient and exact de Bruijn graph representation based on a Bloom filter. Algorithms Mol Biol 8, 22 (2013). https://doi.org/10.1186/1748-7188-8-22 (Year: 2013).*
Melsted, P. et al., "KmerStream: streaming algorithms for K-mer abundance estimation." Bioinformatics, vol. 30, No. 24 2014, pp. 3541-3547.
Sivadan, N. et al., "Kmerlight: fast and accurate k-mer abundance estimation." Computer Science—Data Structures and Algorithms, 2016.

* cited by examiner

*Primary Examiner* — G. Steven Vanni
*Assistant Examiner* — Robert James Kallal

(57) ABSTRACT

A method for characterizing a sample comprising genetic information, comprising: (i) receiving a plurality of sequencing signals from a sequencing operation for a sample, each of the plurality of sequencing signals representing a genetic sequence; (ii) setting, based on a received sequencing signal, a bit within a bit array to a first value for the received sequencing signal, wherein a set of one or more bits is associated with a unique received sequencing signal; (iii) calculating a rate of change of bits within the bit array as new sequencing signals are received; (iv) comparing the rate of change to a predetermined threshold; and (v) identifying the sequencing operation as insufficient if the rate of change is at or above the predetermined threshold, or identifying the sequencing operation as sufficient if the rate of change is at or below the predetermined threshold.

13 Claims, 4 Drawing Sheets

SYSTEM AND METHOD FOR DETERMINING SUFFICIENCY OF GENOMIC SEQUENCING

FIELD OF THE DISCLOSURE

The present disclosure is directed generally to methods and systems for determining the sufficiency of a sequencing operation.

BACKGROUND

Next-generation sequencing (NGS) is an important tool for genomics research, and has numerous applications for discovery, diagnosis, and other methodologies. Nanopore sequencing, for example, makes it possible to determine the composition of long nucleotide sequences by measuring changes in electric current flow through a nanopore as the nucleotide sequences move through the pore. This technology makes it possible to sequence samples in real time, and is increasingly being utilized for wide variety of applications such as diagnostics, drug resistance determination, and epidemiology, among many others.

For many applications, rapid sequencing is of upmost importance. Typical sequencing workflows for nanopore and related technologies, for example, consist of translating the output—such as the detected nanopore current changes— into k-mers, followed by analysis of the resulting sequences. Both steps can take a significant amount of computer resources and computing time. As more and more samples are characterized and stored, there is a need to harness the information and characterize the contents of samples being sequenced as quickly as possible.

In addition to speed, resource utilization and preservation is important. Minimizing the amount of resources used to analyze a sample saves both time and money. For example, one important resource is sequencing machine time. The less time a sequencing machine spends analyzing a sample, the more efficient the sequencing machine and thus the entire sequencing operation.

SUMMARY OF THE DISCLOSURE

There is a continued need for rapid and efficient analysis of next-generation sequencing data to enable identification of nucleic acid in a sample.

The present disclosure is directed to inventive methods and systems for real-time determination of the sufficiency of a next-generation nucleic acid sequencing operation. Various embodiments and implementations herein are directed to a system that receives a sequencing signal from a sequencing operation for a genomic sample. The system adjusts one or more bits in a first bit array or similar data structure to represent the sequencing signal and the genomic sequence that the signal and thus the bit represent. The system determines a rate of change of bits within the bit array over time as new sequencing signals are received, and compares that rate of change to a predetermined or otherwise supplied threshold. If the rate of change is above a predetermined threshold, meaning that the sequencing operation is still obtaining sequencing signals and changing bits at a rate that indicates insufficiency of the sequencing operation, then the sequencing operation is identified as being insufficient. The system might then continue the sequencing operation in an attempt to reach sufficiency. If the rate of change falls below the predetermined threshold, meaning that the sequencing signals obtained by the sequencing operation are repetitive or otherwise indicating sufficiency, then the sequencing operation is identified as being sufficient. The system might then terminate the sequencing operation.

Generally, in one aspect, a method for characterizing a sample comprising genetic information is provided. The method includes the steps of: (i) receiving a plurality of sequencing signals from a sequencing operation for a sample, each of the plurality of sequencing signals representing a genomic sequence; (ii) setting, based on a received sequencing signal, a bit within a bit array to a first value for the received sequencing signal, wherein a set of one or more bits is associated with a unique received sequencing signal; (iii) calculating a rate of change of bits within the bit array as new sequencing signals are received; (v) comparing the rate of change to a predetermined threshold; and (v) identifying the sequencing operation as insufficient if the rate of change is at or above the predetermined threshold, or identifying the sequencing operation as sufficient if the rate of change is at or below the predetermined threshold.

According to an embodiment, the method includes applying a first function to each of the plurality of sequencing signals to generate the received sequencing signal.

According to an embodiment, identifying the sequencing operation as insufficient comprises continuing the sequencing operation.

According to an embodiment, identifying the sequencing operation as sufficient comprises terminating the sequencing operation.

According to an embodiment, calculating a rate of change comprises summing the bits within the bit array.

According to an embodiment, calculating a rate of change comprises comparing a sum of the bits within the bit array to a previous sum of the bits within the bit array.

According to an embodiment, the rate of change of bits within the bit array is calculated using only a subset of the bits within the bit array.

According to an embodiment, the rate of change of bits within the bit array is calculated by performing a bit-wise AND operation with another bit array.

According to an embodiment, the method includes converting each of the sequencing signals from the sequencing operation to a corresponding k-mer.

According to an embodiment, the method includes incrementing the first value for a bit within the bit array to a subsequent value when a subsequent received sequencing signal associated with the bit is generated, wherein the step of calculating a rate of change comprises a consideration of the subsequent value of one or more bits.

According to an embodiment, the sequencing platform is a pore-based sequencing platform.

According to an embodiment, the step of calculating a rate of change of bits within the bit array comprises averaging a plurality of rate change calculations obtained during a predefined time period.

According to another aspect is a system for characterizing a sample comprising genetic information. The system includes sequencing data obtained from the sample; a data structure configured to record the sequencing data; and a processor configured to: (i) set, based on the sequencing data, a bit within the data structure to a first value for the received sequencing signal, wherein a set of one or more bits is associated with a unique received sequencing signal; (ii) calculate a rate of change of bits within the bit array as new sequencing signals are received; (iii) compare the rate of change to a predetermined threshold; and (iv) identify the sequencing operation as insufficient if the rate of change is at or above the predetermined threshold, or identify the sequencing operation as sufficient if the rate of change is at or below the predetermined threshold.

According to an embodiment, the processor is configured to terminate a sequencing operation identified as sufficient.

According to an embodiment, the processor is configured such that the rate of change of bits within the bit array is calculated using only a subset of the bits within the bit array.

According to an embodiment, the processor is configured to calculate the rate of change by averaging a plurality of rate change calculations obtained during a predefined time period.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects as discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments of a system and method for efficiently characterizing a genomic sample using sequencing signals generated by a next-generation sequencing platform. The system, which may optionally comprise a sequencer, receives a sequencing signal from a sequencing operation for the sample and/or retrieves a stored sequencing signal. The system adjusts one or more bits in a first bit array or similar data structure to represent each sequencing signal and the genomic sequence that the signal, and thus the one or more bits, represent. The system determines a rate of change of bits within the bit array over time as new sequencing signals are received, and compares that rate of change to a predetermined or otherwise supplied threshold. If the rate of change is above a predetermined threshold, the sequencing operation is identified as being insufficient. The system might then continue the sequencing operation in an attempt to reach sufficiency. If the rate of change falls is below the predetermined threshold, the sequencing operation is identified as being sufficient. The system might then terminate the sequencing operation. The system and method for characterizing a genomic sample disclosed and described herein can be used with any sequencing platform or system.

Figure 1:
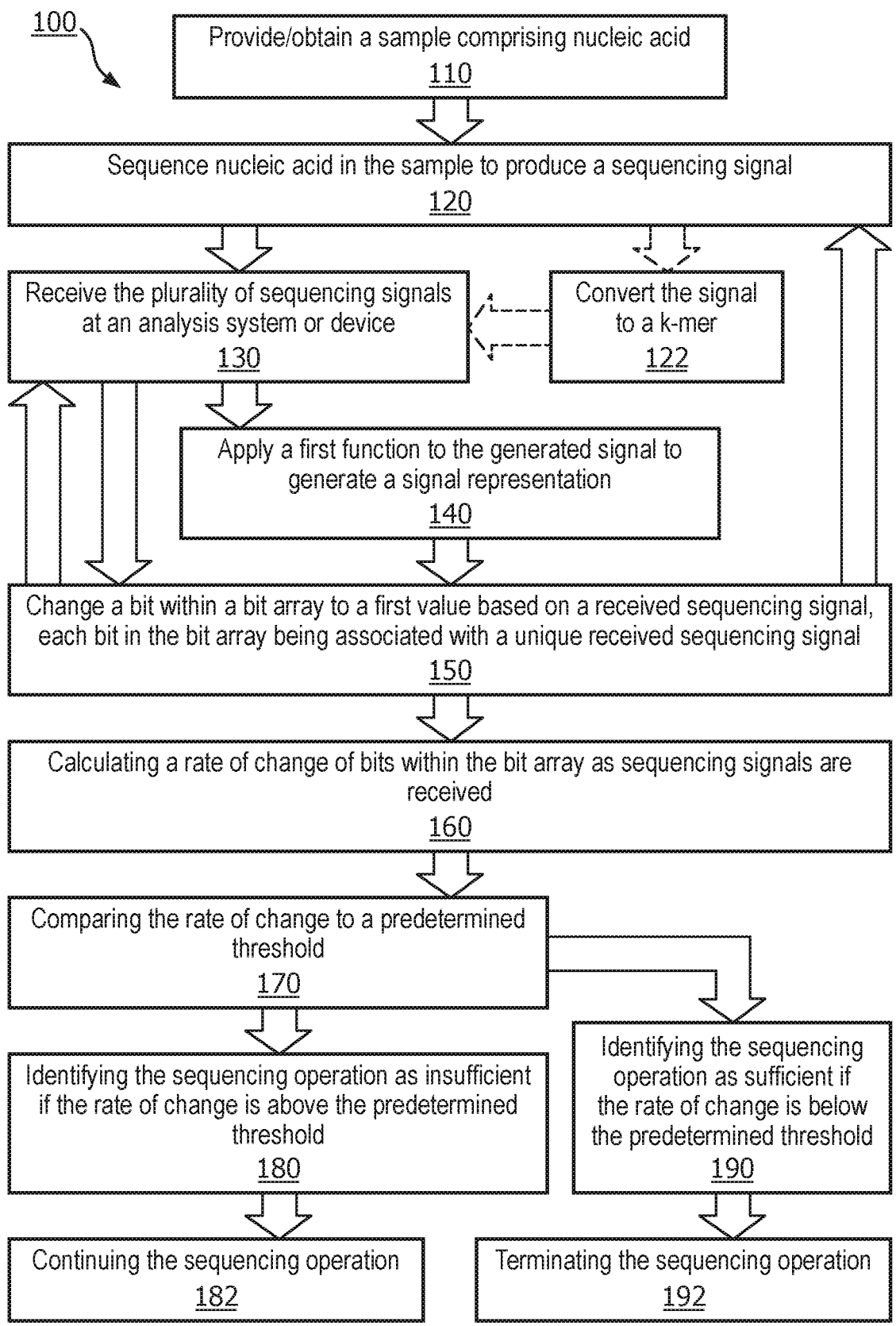
FIG. 1 is a flowchart of a method for characterizing a genomic sample, in accordance with an embodiment.

Referring to FIG. 1, in one embodiment, is a flowchart of a method 100 for characterizing a genomic sample. At step 110 of the method, a sample comprising or potentially comprising nucleic acid to be sequenced is provided or received. The sample may comprise nucleic acid from one or more microorganisms such as bacteria, viruses, fungi, and/or from plants or animals, among many other sources. A sample may comprise nucleic acid molecules from one organism or from multiple organisms. Samples may be obtained in a clinical setting, from the environment, from indoor or outdoor surfaces, or from any other source. It is recognized that there is no limitation to the source of the sample, or the nucleic acid(s) in the sample.

The sample and/or the nucleic acids therein may be prepared for sequencing using any method for preparation, which may be at least in part dependent upon the sequencing platform. According to an embodiment, the nucleic acids may be extracted, purified, and/or amplified, among many other preparations or treatments. For some platforms, the nucleic acid may be fragmented using any method for nucleic acid fragmentation, such as shearing, sonication, enzymatic fragmentation, and/or chemical fragmentation, among other methods, and may be ligated to a sequencing adaptor or any other molecule or ligation partner.

At step 120 of the method, the sequencing platform sequences at least a portion of a nucleic acid from the sample, thereby generating a sequencing signal in real time. The sequencing signal is any signal that represents the sequence of the nucleic acid being sequenced, and can be any signal representative of any sequence, where a genetic or genomic "sequence" is any series of one or more nucleic acid bases obtained by the sequencing platform. The sequencing platform can be any sequencing platform, including but not limited to any systems described or otherwise envisioned herein. For example, the sequencing platform can be a real-time single-molecule sequencing platform, although many other sequencing platforms are possible.

Figure 2:
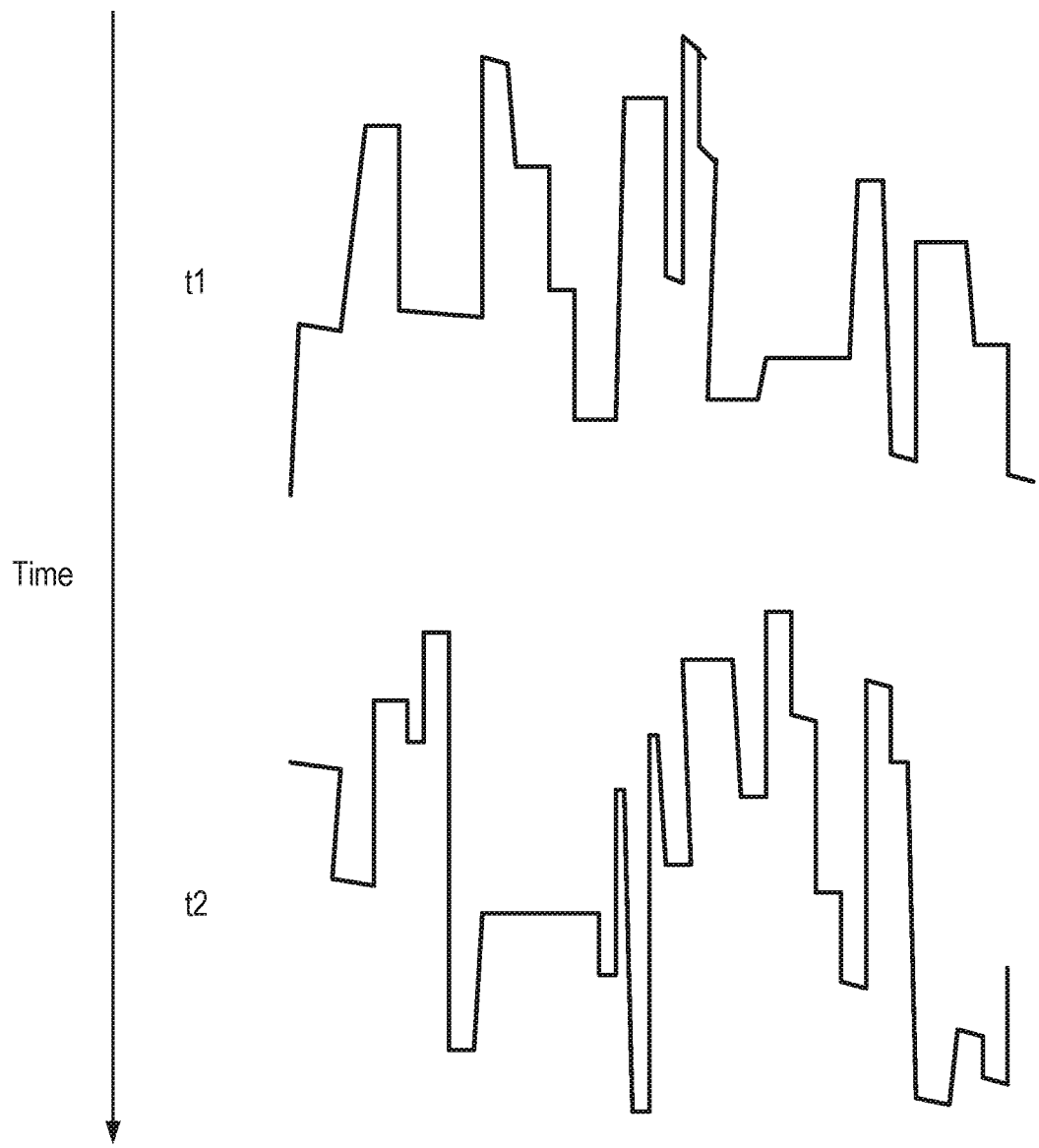
FIG. 2 is a schematic representation of sequencing signals, in accordance with an embodiment.

According to an embodiment, the sequencing platform is a pore-based sequencing platform. As a single nucleic acid strand passes through the pore, the bases affect a current flow through the pore as detected by a current meter. Each type of base (A, C, G, and T) has a slightly different effect on the current flow through the pore, and thus the waveform generated by the changing current flow is representative of the sequence of nucleic acid bases that pass through the pore. An example of two waveforms, t1 and t2, is provided in FIG. 2, which is an approximation or estimate of a shape and/or magnitude of expected current flow signal through the pore generated by the presence of an A, C, G, or T base. In many systems the generated waveform is interpreted to reveal the underlying genomic sequence of the nucleic acid strand that passed through the pore. Many other sequencing platforms are also possible.

At optional step 122 of the method, the generated sequencing signal is converted to a k-mer that represents the underlying genomic sequence of the nucleic acid strand that passed through the pore. For example, the system may comprise a controller or module configured or programmed to convert the signal to a k-mer using known methods for conversion.

The sequencing signal may be utilized immediately for additional steps of the methods described or otherwise envisioned herein, or may be stored for future use by this and other methods. Accordingly, the system may comprise or be in communication with local or remote data storage configured to store the sequencing data. The stored sequencing data may be in the form of waveforms, k-mers, and/or any other form of the sequencing signals generated by the sequencing operation or the system.

At step 130 of the method, the system receives a plurality of sequencing signals from the sequencing operation. According to an embodiment, a sequencing signal is communicated to or from the sequencing platform to a controller or other analysis module for downstream analysis and characterization such as identification of the nucleic acid sequence and/or the sample. For example, according to one embodiment the sequencing platform may comprise a controller or other analysis module for downstream analysis and characterization. According to another embodiment, the sequencing platform communicates the generated sequencing signal, in real-time or at certain time points, to a local or remote controller or other analysis module for downstream analysis and characterization. According to another embodiment, the system receives or retrieves the plurality of sequencing signals from a database of stored sequencing signals.

At optional step 140 of the method, a first function is applied to the generated signal to generate a first signal representation. Alternatively, the first function is applied to the k-mer resulting from interpretation of the signal. The function can be applied to the signal in real-time as it is generated, or can be applied at any point during or after sequencing. The first function can be any function that generates a signal representation that can be utilized by the system in downstream steps of the method. According to an embodiment, the function converts a signal of arbitrary size to a data point of fixed size. A hash function, for example, can convert a signal of arbitrary size to a hash value of fixed size, typically comprising one or more integers, stored in one or more bits. The fixed size can be any size sufficient for, for example, the system to represent the variety of genomic sequences for which the system is designed or programmed.

Figure 3:
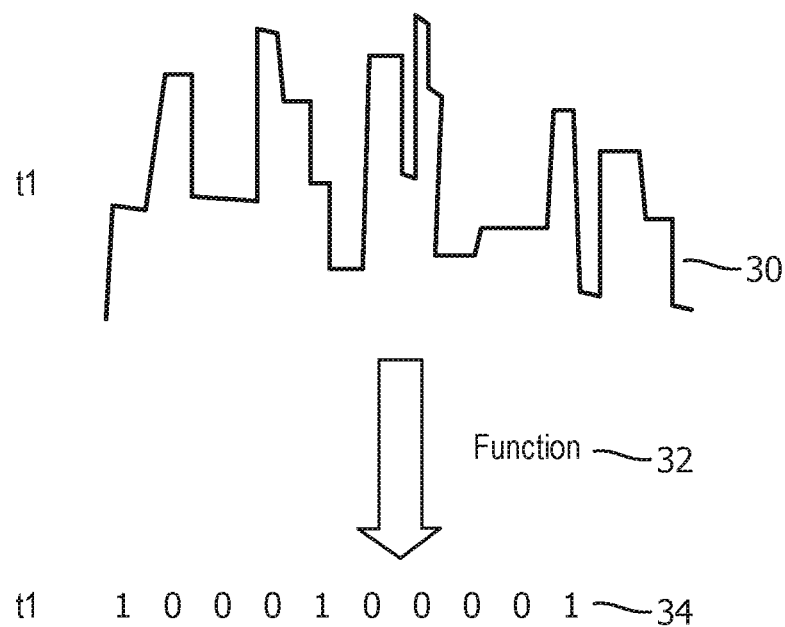
FIG. 3 is a schematic representation of a function applied to a sequencing signal, in accordance with an embodiment.

For example, referring to FIG. 3 is a schematic representation of a function 32 applied to a generated waveform 30 to generate a first waveform representation 34. The function can be a hash function configured to generate one or more bits for a bit array, as shown in FIG. 3, although many other functions are possible. The output of step 140, for example, is therefore a signal representation that can be added to the bit array or other data structure.

As described or otherwise envisioned herein, the data structure can comprise a wide variety of formats and embodiments. For example, the data structure can comprise a bit array comprising an array of bits associated with sequencing signals. According to an embodiment, the data structure can comprise elements within which bits are modified. For example, the data structure could comprise a collection of integers, and the bits in the integers can be manipulated according to the methods and systems described or otherwise envisioned herein. Accordingly, the phrase "bit array" comprises any of the possible data structures that can be utilized to represent received genomic sequences, and "bit" comprises any of the elements within the data structures that can be adjusted, altered, or otherwise changed to represent a received genomic sequence.

At step 150 of the method, one or more bits within a bit array or other data structure are set to a new value based on the received sequencing signal and/or the generated signal representation from the first function. The one or more bit values are associated with the sequencing signal, with each sequencing signal recognized by the system associated with a unique set of one or more bit values.

When a new sequencing operation commences, the values within a bit array such as a Bloom filter can be set to zero (0), indicating that the data structure has not yet recorded any sequences. As a sequencing signal is received or obtained by the system and processed to be logged within the data structure, the set of one or more bits associated with that sequencing signal are changed to one (1). Early in the sequencing operation most bits will be set to zero since few sequencing signals have been received and logged. As the sequencing operation progresses and more sequencing signals have been logged, more bits are set to one. The longer the sequencing operation progresses, fewer new (i.e., unlogged) sequencing signals are received and thus the rate of new bits being set to 1 drops and eventually approaches zero.

Figure 4:
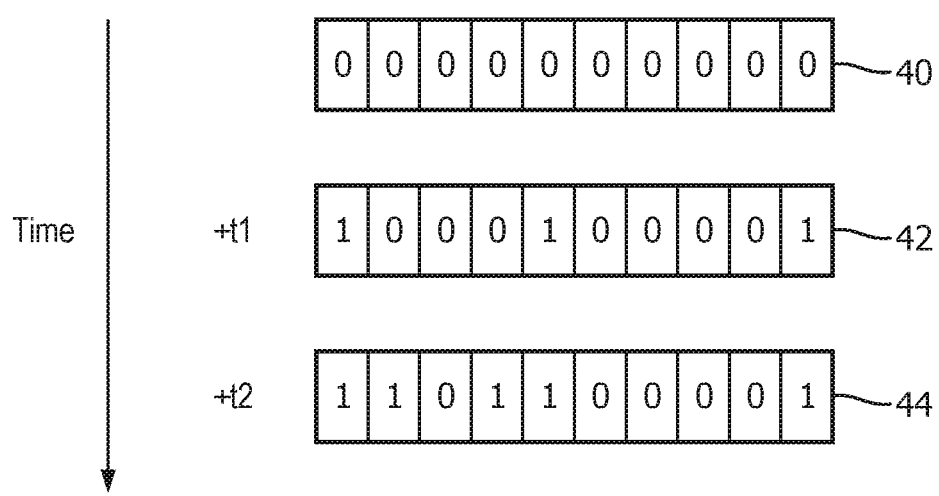
FIG. 4 is a schematic representation of a data structure comprising one or more sequencing signal representations, in accordance with an embodiment.

For example, referring to FIG. 4 is a schematic representation of two generated waveform representations, t1 and t2, being added to a bit array 40. According to an embodiment, bit array 40 is a Bloom filter or a counting Bloom filter. Initially the bit array 40 will comprise no waveform representations. When t1 is added to bit array 40, one or more bits in bit array 40 are changed. In this example, one or more bits are changed from "0" to "1" to represent the waveform representation 34 (i.e., t1). Accordingly, bit array 42 comprises waveform representation 34. When t2 is added to bit array 42, one or more bits in bit array 42 are changed from "0" to "1" to represent the waveform representation for t2. Accordingly, bit array 44 comprises both waveform representations t1 and t2. As the sequencing continues and new waveform representations representing k-mers or waveforms are detected, more bits in the bit array will be changed. Notably, the function can be performed and the waveform representation can be integrated into the bit array in real-time as the sequencer generates a waveform.

Instead of a Bloom filter, a counting Bloom filter can be used to track the number of times a sequencing signal has been observed, up to a certain threshold. Accordingly, sequencing signals that correspond to errors can be ignored. Assuming that they are random, they will appear as rare sequencing signals.

According to an embodiment, the system returns to step 130 to receive a second sequencing signal from the sequencing operation for the sample, the second sequencing signal representing a second genomic sequence. Alternatively, the system returns to step 130 to retrieve a second sequencing signal from a database of stored sequencing signals. The system can apply the first function to the second sequencing signal to generate a second signal representation at step 140 of the method, and can set, based on the sequencing signal and/or second signal representation, one or more bits within the bit array to a new value. In this way, the bit array can accumulate any number of genomic sequences, from one to many sequences. The system can be programmed, designed, or otherwise controlled to obtain a certain number or quantity of sequences, ranging from one to two or more.

According to an embodiment, the system increments the one or more bit values for a corresponding sequencing signal or signal representation to a subsequent or incremental value when a subsequent received sequencing signal associated with the one or more bits is received. Alternatively, the system may comprise a counter that counts the number of a specific received sequencing signal or generated signal representation, which thus represents a number of times that a specific genomic sequence is sequenced or obtained by the system.

According to one embodiment, the system can monitor the progress of a sequencing analysis. For example, by monitoring the rate that new values in the bit array are changed, it is possible to estimate whether the sequencing process is reaching a saturation point. If values are frequently changed in the bit array as signal representations are added, new genomic sequences are being obtained. If signal representations are added to the bit array without a change in bit values, then repetitive genomic sequences are being obtained.

Thus, at step 160 of the method, the system calculates a rate of change of bits within the bit array as new sequencing signals are received. According to an embodiment, the system calculates the rate of change of bits within the bit array by summing all the bits in the array, and comparing the sum to a previous sum of all the bits in the array. For example, the sum of the bits of array 40 in FIG. 4 is zero (0), and the sum of the bits of array 44 in FIG. 4 is five (5). Thus the rate change from array 40 to array 44 is five (5). According to an embodiment, bits in the bit array are only changed to a first value if the unique genomic sequence those bits are associated with are found in a sequencing signal for the first time. As that genomic sequence is obtained a second, third, or more times, the bits in the bit array associated with that genomic sequence are not changed or incremented because the sequence was already logged in the data structure. In this way, the data structure may not quantify the genomic sequences, but may only determine that they are present. According to another embodiment, bits in the bit array are only changed to a first value if the unique genomic sequence those bits are associated with are found in a sequencing signal for the n-th time, with n greater than one. As that genomic sequence is obtained an n+1-th time, or more times, the bits in the bit array associated with that genomic sequence are not changed or incremented because the sequence was already logged in the data structure. In this way, the data structure may determine that the genomic sequences are present and are not error sequences, which are expected to be rare.

The rate can be obtained continuously (i.e., as each new sequencing signal is added to the array) or can be obtained periodically using a determined periodicity. The rate can obtained at user-derived intervals, which may by defined by or otherwise depend at least in part on the speed, efficiency, or other needs of the user. For example, a user may lower the rate calculation frequency if less speed or more accurate determination of rate is needed, or may raise the rate calculation frequency if more speed or less accurate determination of rate is needed. Notably, the sum may not change if a genomic sequence has already been logged by the bit array, meaning that the bits associated with that genomic sequence have already been changed to the first value. In this instance, the difference between the current sum and the previous sum may be zero. This may not indicate that the sequencing operation is complete or sufficient or approaching saturation, only that a sequence has been obtained more than once. Accordingly, the rate calculation may be designed or set to obtain and/or factor multiple readings over time.

According to another embodiment, the system calculates the rate of change of bits within the bit array by incrementing the first value for a bit within the bit array to a subsequent value when a subsequent received sequencing signal associated with the bit is generated. In other words, when a genomic sequence is obtained for a second time (and subsequent times), the bit value in the bit array associated with that genomic sequence can be incremented. Alternatively, a counter associated with the bit or bits in the bit array associated with each obtained and recorded genomic sequence can be incremented as a subsequent received sequencing signal associated with the bit or bits in the bit array is generated and logged in the bit array. Accordingly, calculating the rate of change comprises a consideration of the incremented bit values, and/or a consideration of the counter associated with the bit or bits in the bit array. For example, the system may sum or otherwise factor in the incremented bit values or counts associated with the bit array.

According to an embodiment, the rate may be time-averaged to determine a rate of change over a period of time rather than as each genomic sequence is logged in or otherwise added to the bit array. For example, as described above, a rate change calculation may indicate no change, or little change, if a newly-obtained sequence has already been logged by the bit array. Since this may not indicate that the sequencing operation is complete or sufficient or approaching saturation, only that a particular sequence has been obtained more than once (something that is expected to happen often but with increasing frequency as the sequencing operation proceeds), the system may be programmed, designed, or otherwise set to obtain and/or factor multiple readings over time in order to calculate a rate. The amount of readings, and/or the amount of time, obtained by the system and used in the rate calculation can be predetermined or can be a user setting.

According to an embodiment, the rate of change of bits within the bit array is calculated using only a subset of the bits within the bit array. The system or user may only be interested in a subset of sequences or species within the data structure, and thus will only examine sufficiency or insufficiency of the subset of interest. As an example, a data structure may be configured to recognize two or more organisms, different species, different genomes, or other different contributors to a sample, but for any one use or sequencing operation the user may only be interested in a subset of the possible sequences within the data structure. As yet another example, the subset of bits within the bit array used for the rate calculation may be target genes or genomic regions such as resistance genes or other genes of interest. An another example, the sequencing operation may be designed to identify or otherwise obtain sufficient sequencing data from an under-represented species or contributor in a sample, which would require more sequencing signals to be obtained during the sequencing operation. As a result, a rate threshold must be selected that allows greater repetition of sequences to be obtained such that the minor contributor is sufficiently sampled. Many other examples and subsets are possible. According to an embodiment, the rate of change of bits within the bit array is calculated by performing a bit-wise AND operation with another bit array.

In addition to the methods described above, there are other possible methods for determining the rate of change of information within the data structure.

At step 170 of the method, the system compares the calculated rate of change to a predetermined rate threshold. The system can continuously compare the calculated rate to a predetermined rate threshold or can periodically compare the calculated rate to a predetermined rate threshold. The comparison can comprise, for example, a simple subtraction of the calculated rate from the predetermined rate threshold (or vice versa) using the negative/positive result to determine whether a calculated rate falls under the threshold, is equal to the threshold, or is above the threshold. Alternatively or additionally the system may quantify the difference between the calculated rate and the predetermined rate threshold, which may allow the system to track whether the calculated rate is approaching the threshold over a period of time.

Rate may be expressed in units defined by the settings of the system, including sampling frequency. For example, rate may be expressed as the number of bits that have been changed over the time period between rate calculations or a time-averaged calculation period, such as 543 bits/period, where "period" is a time period such as seconds, a minute, 5 minutes, and so on.

The predetermined rate threshold can be determined by a user or can be a default value. In the case of a user-set threshold, the user may determine the threshold by experimental testing, via a user interface of the system, by providing parameters that are used to define a threshold, and/or by a variety of other mechanisms. A default threshold may be determined by programming, the samples being processed, and/or by a variety of other mechanisms. For example, if the goal of the sequencing operation is to obtain sequencing data with as much accuracy in sampling or coverage as possible, a rate threshold will be selected that allows for a low rate of change. In other words, the system allows fewer bits to be changed by the bit array because fewer novel sequencing signals will be added to the data structure over time as the coverage or accuracy demands are increased.

As another example, if the goal of the sequencing operation is to quickly obtain an identification of the organism or organisms within a sample, the threshold may be set high such that a slowdown in novel genomic sequences indicates that there is sufficient data for an identification and the sequencing operation can be terminated to save both time and resources.

The predetermined rate threshold can be experimentally or otherwise quantitatively derived. For example, the bit array can track when all portions of the genome, or all possible sequencing signals, have been logged into the data structure, indicating a 1× coverage. The time period required to obtain 1× coverage can be utilized to calculate the amount of time needed to obtain 10×, 30×, or any amount of coverage. This amount of time can factor into the rate calculation and/or the rate threshold.

At steps 180 and 190 of the method, the system uses the output of the comparison of the calculated rate of change to a predetermined rate threshold to evaluate the sequencing operation. Specifically, the system uses the output of the comparison to identify the current state of the sequencing operation as either insufficient or sufficient.

According to an embodiment, at step 180 of the method, the system identifies the current state of the sequencing operation as insufficient if the calculated rate of change is above the predetermined threshold. According to one embodiment, a sequencing operation might be identified as insufficient if the calculated rate of change equals the predetermined threshold.

Insufficiency of the sequencing operation can be defined as a state or stage of the sequencing operation wherein there is unlikely to be an adequate amount of sequencing data recorded or logged in the data structure for the ultimate purpose(s) or goal(s) of that sequencing operation. Insufficiency depends on one or more of a variety of factors including the purpose(s) or goal(s) of that sequencing operation, one or more user settings, parameters of the sequencing operation, the source of the sample, the likely and/or known source(s) of genetic information in the sample, and many other possible factors. For example, the sequencing operation can be deemed insufficient if there is unlikely to be: adequate sequencing data to identify a contributor or multiple contributors to a sample, adequate sequencing data to obtain the desired coverage and/or depth of the sequence, adequate sequencing data to obtain data from a minor contributor in the sample, or adequate sequencing data to otherwise achieve a goal or purpose of the sequencing operation.

According to an embodiment, the system may only require a single comparison fall above the predetermined threshold to declare the sequencing operation insufficient. Alternatively, the system may require multiple comparisons—sequentially, in total, and/or during a time period, for example—before declaring the sequencing operation insufficient. This may be a user setting, may be a system setting, or may be experimentally derived, among other possible determinations. For example, the amount of rate comparisons falling above the predetermined threshold may depend on the sample, the purpose(s) or goal(s) of the sequencing operation, and/or a variety of other factors. The amount of rate comparisons allowed to fall above the predetermined threshold before making a determination of insufficiency may also depend in part on timing of the rate comparisons. For example, the number of rate comparisons falling above the predetermined threshold before making a determination of insufficiency may be allowed to increase or decrease as the sequencing operation progresses.

At step 182 of the method, if the system declares the sequencing operation insufficient based on the one or more comparisons of the calculated rate change(s) to the rate change threshold, the system instructs the sequencing operation to continue (or fails to instruct the sequencing operation to terminate). Thus, the sequencing operation will continue, additional sequencing data will be obtained and logged in the bit array, and one or more steps of the method described or otherwise envisioned herein will repeat in an attempt to achieve sufficiency of the sequencing operation.

At step 190 of the method, the system identifies the current state of the sequencing operation as sufficient if the calculated rate of change is below the predetermined threshold. According to one embodiment, a sequencing operation might be identified as sufficient if the calculated rate of change equals the predetermined threshold.

Sufficiency of the sequencing operation can be defined as a state or stage of the sequencing operation wherein there is likely to be an adequate amount of sequencing data recorded or logged in the data structure for the ultimate purpose(s) or goal(s) of that sequencing operation. Sufficiency depends on one or more of a variety of factors including the purpose(s)

or goal(s) of that sequencing operation, one or more user settings, parameters of the sequencing operation, the source of the sample, the likely and/or known source(s) of genetic information in the sample, and many other possible factors. For example, the sequencing operation can be deemed sufficient if there is likely to be: adequate sequencing data to identify a contributor or multiple contributors to a sample, adequate sequencing data to obtain the desired coverage and/or depth of the sequence, adequate sequencing data to obtain data from a minor contributor in the sample, or adequate sequencing data to otherwise achieve a goal or purpose of the sequencing operation.

According to an embodiment, the system may only require a single comparison fall below the predetermined threshold to declare the sequencing operation sufficient. Alternatively, the system may require multiple comparisons—sequentially, in total, and/or during a time period, for example—before declaring the sequencing operation sufficient. This may be a user setting, may be a system setting, or may be experimentally derived, among other possible determinations. For example, the amount of rate comparisons falling below the predetermined threshold may depend on the sample, the purpose(s) or goal(s) of the sequencing operation, and/or a variety of other factors. The amount of rate comparisons allowed to fall below the predetermined threshold before making a determination of sufficiency may also depend in part on timing of the rate comparisons. For example, the number of rate comparisons falling below the predetermined threshold before making a determination of sufficiency may be allowed to increase or decrease as the sequencing operation progresses.

At step 192 of the method, if the system declares the sequencing operation sufficient based on the one or more comparisons of the calculated rate change(s) to the rate change threshold, the system instructs the sequencing operation to terminate (or fails to instruct the sequencing operation to continue). Thus, the sequencing operation will terminate, and no additional sequencing data will be obtained and logged in the bit array. The universe of sequencing data for the specific sequencing operation will be now already logged in the data structure.

Once the sequencing operation is terminated and the universe of sequencing data for the specific sequencing operation is logged in the data structure, that data can be utilized for any of a variety of goals or purposes. For example, the information may be used to identify one or more contributors to a sample. As another example, the information may be used to identify specific genes, alleles, or other genetic information in a sample, person, location, or other source. A clinician, for example, may use the information from the terminated sequencing operation to identify or diagnose a pathogen, or to identify an allele or genetic disorder in a patient, among many other possible uses.

Figure 5:
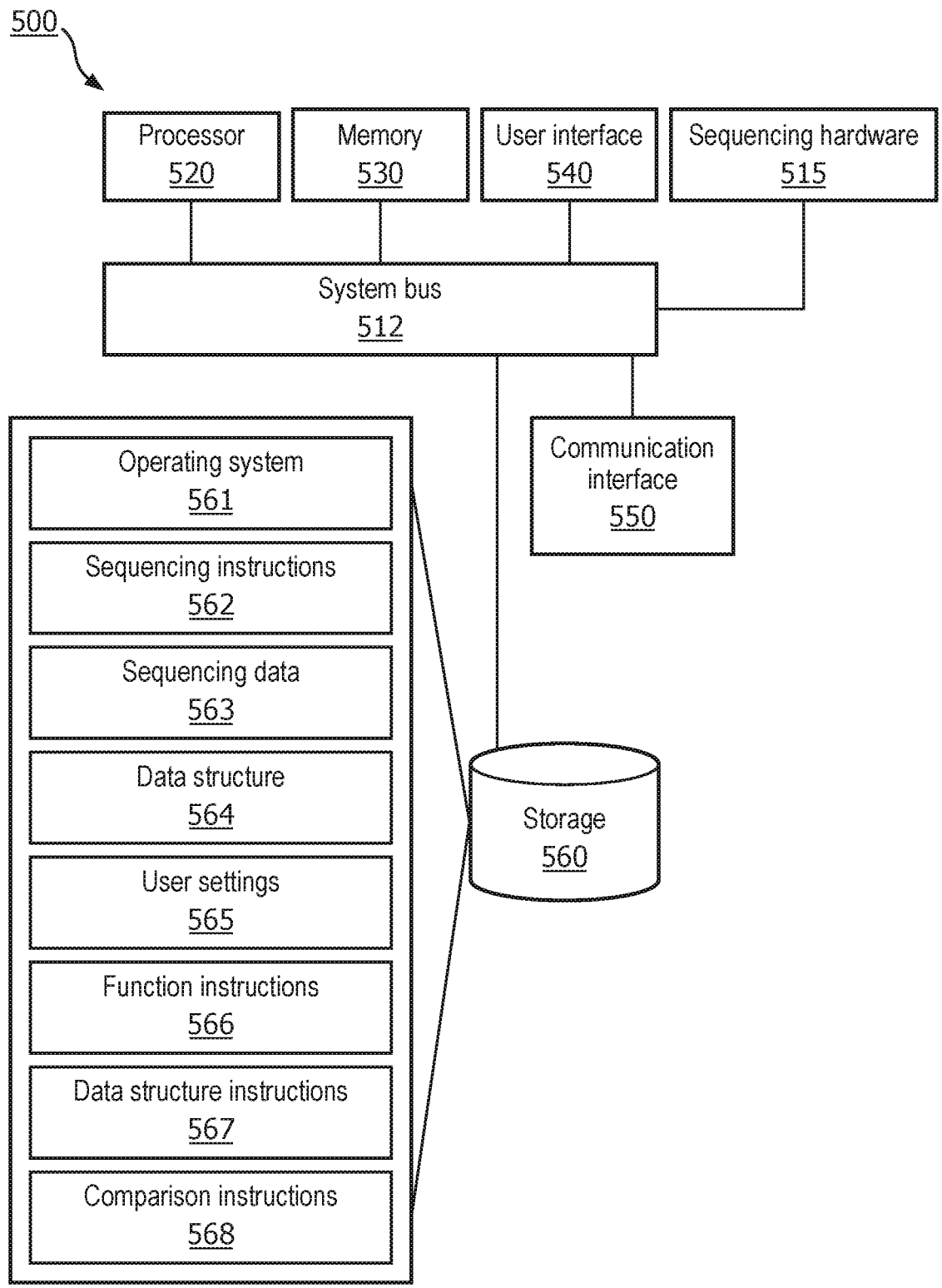
FIG. 5 is a schematic representation of a sequence characterization system, in accordance with an embodiment.

Referring to FIG. 5, in one embodiment, is a schematic representation of a system 500 for analyzing a sequencing operation. System 500 may be any of the systems described or otherwise envisioned herein, and may comprise any of the components described or otherwise envisioned herein.

According to an embodiment, system 500 comprises one or more of a processor 520, memory 530, user interface 540, communications interface 550, and storage 560, interconnected via one or more system buses 512. In some embodiments, such as those where the system comprises or directly implements a sequencer or sequencing platform, the hardware may include additional sequencing hardware 515 such as a real-time single-molecule sequencer, including but not limited to a pore-based sequencer, although many other sequencing platforms are possible. It will be understood that FIG. 5 constitutes, in some respects, an abstraction and that the actual organization of the components of the system 500 may be different and more complex than illustrated.

According to an embodiment, system 500 comprises a processor 520 capable of executing instructions stored in memory 530 or storage 560 or otherwise processing data to, for example, perform one or more steps of the method. Processor 520 may be formed of one or multiple modules. Processor 520 may take any suitable form, including but not limited to a microprocessor, microcontroller, multiple microcontrollers, circuitry, field programmable gate array (FPGA), application-specific integrated circuit (ASIC), a single processor, or plural processors.

Memory 530 can take any suitable form, including a non-volatile memory and/or RAM. The memory 530 may include various memories such as, for example L1, L2, or L3 cache or system memory. As such, the memory 530 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 500. It will be apparent that, in embodiments where the processor implements one or more of the functions described herein in hardware, the software described as corresponding to such functionality in other embodiments may be omitted.

User interface 540 may include one or more devices for enabling communication with a user. The user interface can be any device or system that allows information to be conveyed and/or received, and may include a display, a mouse, and/or a keyboard for receiving user commands. In some embodiments, user interface 540 may include a command line interface or graphical user interface that may be presented to a remote terminal via communication interface 550. The user interface may be located with one or more other components of the system, or may located remote from the system and in communication via a wired and/or wireless communications network.

Communication interface 550 may include one or more devices for enabling communication with other hardware devices. For example, communication interface 550 may include a network interface card (NIC) configured to communicate according to the Ethernet protocol. Additionally, communication interface 550 may implement a TCP/IP stack for communication according to the TCP/IP protocols. Various alternative or additional hardware or configurations for communication interface 550 will be apparent.

Storage 560 may include one or more machine-readable storage media such as read-only memory (ROM), random-access memory (RAM), magnetic disk storage media, optical storage media, flash-memory devices, or similar storage media. In various embodiments, storage 560 may store instructions for execution by processor 520 or data upon which processor 520 may operate. For example, storage 560 may store an operating system 561 for controlling various operations of system 500. Where system 500 implements a sequencer and includes sequencing hardware 515, storage 560 may include sequencing instructions 562 for operating the sequencing hardware 515, and sequencing data 563 obtained by the sequencing hardware 515. Storage 560 may also store a data structure 564, user settings 565, and other elements.

It will be apparent that various information described as stored in storage 560 may be additionally or alternatively stored in memory 530. In this respect, memory 530 may also be considered to constitute a storage device and storage 560 may be considered a memory. Various other arrangements will be apparent. Further, memory 530 and storage 560 may both be considered to be non-transitory machine-readable media. As used herein, the term non-transitory will be understood to exclude transitory signals but to include all forms of storage, including both volatile and non-volatile memories.

While system 500 is shown as including one of each described component, the various components may be duplicated in various embodiments. For example, processor 520 may include multiple microprocessors that are configured to independently execute the methods described herein or are configured to perform steps or subroutines of the methods described herein such that the multiple processors cooperate to achieve the functionality described herein. Further, where one or more components of system 500 is implemented in a cloud computing system, the various hardware components may belong to separate physical systems. For example, processor 520 may include a first processor in a first server and a second processor in a second server. Many other variations and configurations are possible.

According to an embodiment, storage 560 of sample characterization system 500 may store one or more algorithms and/or instructions to carry out one or more functions or steps of the methods described or otherwise envisioned herein. For example, processor 520 may comprise one or more of sequencing instructions 562, function instructions 566, data structure instructions 567, and/or comparison instructions 568, among other instructions.

According to an embodiment, sequencing instructions 562 direct the system to operate a sequencing platform such as sequencing hardware 515. This may include any information necessary to process a sample and to generate and obtain sequencing data 563 from the sequencing platform. Sequencing instructions 562 may also instruct the system to communicate sequencing data 563 to another component of system 500. Additionally, sequencing instructions 562 may direct the system to store the sequencing data 563 in a local or remote database for retrieval and use by the system. The database may be located with system 500 or may be located remote from the system, such as in cloud storage and/or other remote storage.

According to an embodiment, function instructions 566 direct the system to apply a function to a generated sequencing signal to generate a first signal representation of that sequencing signal. The function instructions 566 may optionally apply the first function to a k-mer resulting from interpretation of the sequencing signal. The function can be applied to the sequencing signal in real-time as it is generated, or can be applied at any point during or after sequencing. The function can be any function that generates a signal representation. According to an embodiment, the function converts a signal of arbitrary size to a data point of fixed size. A hash function, for example, can convert a signal of arbitrary size to a hash value of fixed size, typically comprising one or more integers. The fixed size can be any size sufficient for, for example, the system to represent the variety of genomic sequences for which the system is designed or programmed.

The function instructions 566 may direct the system to store the generated signal representations in a local or remote database for retrieval and use by the system. The database may be located with system 500 or may be located remote from the system, such as in cloud storage and/or other remote storage.

According to an embodiment, data structure instructions 567 direct the system to record or log a received or retrieved sequencing signal and/or generated signal representation (representative of the received or retrieved sequencing signal) within the data structure. For example, data structure instructions 567 direct the system to set one or more bits within a bit array or other data structure to a new value based on the sequencing signal. The one or more bit values are associated with the sequencing signal, with each sequencing signal recognized by the system associated with a unique set of one or more bit values.

According to an embodiment, data structure instructions 567 also direct the system to calculate the rate of change of bits within the data structure as new sequencing signals are received. According to an embodiment, the system calculates the rate of change of bits within a bit array by summing all the bits in the array, and comparing the sum to a previous sum of all the bits in the array. The data structure instructions 567 can direct the system to calculate the rate continuously (i.e., as each new sequencing signal is added to the array) or can be obtained periodically using a determined periodicity. The rate can obtained at user-derived intervals, which may by defined by or otherwise depend at least in part on the speed, efficiency, or other needs of the user. For example, a user may lower the rate calculation frequency if less speed or more accurate determination of rate is needed, or may raise the rate calculation frequency if more speed or less accurate determination of rate is needed. According to another embodiment, the rate of change of bits within the bit array is calculated using only a subset of the bits within the bit array. The rate may be time-averaged to determine a rate of change over a period of time rather than as each genomic sequence is logged in or otherwise added to the bit array.

These and other user-provided settings, instructions, or information can be stored as user settings 565 in storage 560. According to an embodiment, the user settings are uploaded to the system or provided via the user interface. Additionally, data structure instructions 567 can direct the system to store the result of the rate change calculation in a local or remote database for retrieval and use by the system.

According to an embodiment, comparison instructions 568 direct the system to compare the calculated rate of change to a predetermined rate threshold. The system can continuously compare the calculated rate to a predetermined rate threshold or can periodically compare the calculated rate to a predetermined rate threshold. Alternatively or additionally, the comparison instructions 568 may direct the system to quantify the difference between the calculated rate and the predetermined rate threshold, which may allow the system to track whether the calculated rate is approaching the threshold over a period of time. According to an embodiment, the comparison instructions 568 direct the system to store the result of the comparison in a local or remote database for retrieval and use by the system.

The predetermined rate threshold can be determined by a user or can be a default value, and may be stored in storage 560 as user settings 565. In the case of a user-set threshold, the user may determine the threshold by experimental testing, via a user interface of the system, by providing parameters that are used to define a threshold, and/or by a variety of other mechanisms. A default threshold may be determined by programming, the samples being processed, and/or by a variety of other mechanisms.

According to an embodiment, the comparison instructions 568 direct the system to identify the sequencing operation as insufficient if the calculated rate of change is above the predetermined threshold, or sufficient if the calculated rate of change is below the predetermined threshold. This determination can be stored in local or remote storage and/or communicated locally or remotely, such as via user interface 540.

The comparison instructions 568 direct the system to continue the sequencing operation if the sequencing operation is determined to be insufficient based on the one or more comparisons of the calculated rate change(s) to the rate change threshold. Thus, the sequencing operation will continue, additional sequencing data will be obtained and logged in the bit array, and one or more steps of the method described or otherwise envisioned herein will repeat in an attempt to achieve sufficiency of the sequencing operation.

The comparison instructions 568 direct the system to terminate the sequencing operation if the sequencing operation is determined to be sufficient based on the one or more comparisons of the calculated rate change(s) to the rate change threshold. Thus, the sequencing operation will terminate, and no additional sequencing data will be obtained and logged in the bit array. The universe of sequencing data for the specific sequencing operation will be now already logged in the data structure.

When the sequencing is terminated, or optionally at any point during the sequencing operation, the system can utilize the information within the data structure 564. For example, the information may be used to identify one or more contributors to a sample. As another example, the information may be used to identify specific genes, alleles, or other genetic information in a sample, person, location, or other source. A clinician, for example, may use the information from a sequencing operation, within the data structure, to identify or diagnose a pathogen, or to identify an allele or genetic disorder in a patient, among many other possible uses. According to an embodiment, a healthcare professional may utilize the information from a sequencing operation, within the data structure, to select and implement treatment or care of the surface, individual, animal, or other source of the sample from which the identified species, substrain, or organism was made.

The sample analysis system and method described or otherwise envisioned herein provides numerous advantages over existing systems. For example, the system improves the efficiency and speed with which an organism(s) within a sample are identified. According to an embodiment, the system improves efficiency and speed by reducing the amount of time a sequencing operation runs, thereby reducing the resources used by the sequencing hardware, including operation time and energy. As an example, a sequencing operation utilizing the present system and method can obtain the same information—such as an identification of one or more contributors to a sample—as a sequencing operation that isn't using the present system and method, but it will do it in a much quicker and more efficient timeframe. This frees the sequencing hardware for other operations. In a clinical setting where genomic analysis is become increasingly important, minimizing sequencing time while ensuring sequencing sufficiency is extremely beneficial and valuable. More samples can be analyzed in a shorter amount of time, thereby enabling faster diagnosis and treatment, which can significantly improve treatment outcomes. Rather than forcing patients and clinicians to wait for hours or days in line for a traditional genomic analysis which would enable targeted treatment, the system and method described or otherwise envisioned herein reduces overall wait times and improves the efficiency and speed of the sequencing hardware and center, thereby providing information to a clinician in a timeframe that promotes faster diagnosis, treatment, and thus faster and better treatment response.

For example, in a clinical setting in which an individual is fighting an infection, quickly and accurately identifying the pathogen(s) participating in the infection can lead to faster and more accurate treatment. This can mean the difference between life and death in many settings and/or with many infections. Using the approach and/or system described or otherwise envisioned herein, a clinician or other healthcare provider can make significantly improved and more informed decisions, and can better treat dangerous and often life-threatening infections.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for characterizing a sample comprising genetic information, comprising:
    receiving a plurality of sequencing signals from a sequencing operation for a sample, each of the plurality of sequencing signals representing a genomic sequence;
    setting, based on a received sequencing signal, a bit within a bit array to a first value for the received sequencing signal, wherein a set of one or more bits is associated with a unique received sequencing signal;
    calculating a rate of change of bits within the bit array as new sequencing signals are received during the sequencing operation;
    comparing the rate of change to a predetermined threshold;
    identifying the sequencing operation as insufficient if the rate of change is above the predetermined threshold, or identifying the sequencing operation as sufficient if the rate of change is below the predetermined threshold, and
    continuing the sequencing operation based on identifying the sequencing operation as sufficient or terminating the sequencing operation based on identifying the sequencing operation as insufficient.

2. The method of claim 1, further comprising the step of applying a first function to each of the plurality of sequencing signals to generate the received sequencing signal.

3. The method of claim 1, wherein calculating a rate of change comprises summing the bits within the bit array.

4. The method of claim 3, wherein calculating a rate of change comprises comparing a sum of the bits within the bit array to a previous sum of the bits within the bit array.

5. The method of claim 1, wherein the rate of change of bits within the bit array is calculated using only a subset of the bits within the bit array.

6. The method of claim 1, wherein calculating a rate of change comprises performing a bit-wise AND operation with another bit array.

7. The method of claim 1, further comprising the step of incrementing the first value for a bit within the bit array to a subsequent value when a subsequent received sequencing signal associated with the bit is generated, wherein the step of calculating a rate of change comprises a consideration of the subsequent value of one or more bits.

8. The method of claim 1, wherein the sequencing platform is a pore-based sequencing platform.

9. The method of claim 1, wherein the step of calculating a rate of change of bits within the bit array comprises averaging a plurality of rate change calculations obtained during a predefined time period.

10. A system for characterizing a sample comprising genetic information, comprising:
    sequencing data obtained from the sample;
    a data structure configured to record the sequencing data; and
    a processor configured to:
       (i) set, based on the sequencing data, a bit within the data structure to a first value for the received sequencing signal, wherein a set of one or more bits is associated with a unique received sequencing signal;
       (ii) calculate a rate of change of bits within the bit array as new sequencing signals are received during the sequencing operation;
       (iii) compare the rate of change to a predetermined threshold;
       (iv) identify the sequencing operation as insufficient if the rate of change is above the predetermined threshold, or identify the sequencing operation as sufficient if the rate of change is below the predetermined threshold, and
       (v) continue the sequencing operation based on identifying the sequencing operation as sufficient or terminate the sequencing operation based on identifying the sequencing operation as insufficient.

11. The system of claim 10, wherein the processor is configured to terminate a sequencing operation identified as sufficient.

12. The system of claim 10, wherein the processor is configured such that the rate of change of bits within the bit array is calculated using only a subset of the bits within the bit array.

13. The system of claim 10, wherein the processor is further configured to calculate the rate of change by averaging a plurality of rate change calculations obtained during a predefined time period.

* * * * *